(12) United States Patent
Haar et al.

(10) Patent No.: US 6,787,109 B2
(45) Date of Patent: Sep. 7, 2004

(54) TEST ELEMENT ANALYSIS SYSTEM

(75) Inventors: Hans-Peter Haar, Wiesloch (DE); George B. K. Meacham, Shaker Heights, OH (US)

(73) Assignee: Roche Diagnostics Corporation, Indianapolis, IN (US)

( * ) Notice: Subject to any disclaimer, the term of this patent is extended or adjusted under 35 U.S.C. 154(b) by 238 days.

(21) Appl. No.: 09/896,965

(22) Filed: Jun. 29, 2001

(65) Prior Publication Data

US 2002/0037238 A1 Mar. 28, 2002

(30) Foreign Application Priority Data

Jul. 1, 2000 (DE) .......................................... 100 32 015

(51) Int. Cl.[7] .............................................. G01N 33/48
(52) U.S. Cl. ........................ 422/82.05; 422/58; 422/61; 422/68.1; 436/164
(58) Field of Search ........................... 422/58, 61, 68.1, 422/82.05; 436/63, 164

(56) References Cited

U.S. PATENT DOCUMENTS

| | | | |
|---|---|---|---|
| 4,338,174 A | 7/1982 | Tamura | 204/195 |
| 4,720,372 A | * 1/1988 | Fey et al. | 422/67 |
| 5,035,862 A | 7/1991 | Dietze et al. | 422/68.1 |
| 5,405,511 A | * 4/1995 | White et al. | 205/777.5 |
| 5,972,715 A | 10/1999 | Celentano et al. | 436/164 |
| 6,061,128 A | * 5/2000 | Zweig et al. | 356/243.4 |

* cited by examiner

Primary Examiner—Lyle A. Alexander
(74) Attorney, Agent, or Firm—Sujatha Subramaniam; Roche Diagnostics Corporation

(57) ABSTRACT

Analysis system for the analytical investigation of a sample, in particular of a body fluid. It consists of test elements brought into contact, for performing an analysis, with a sample to be investigated, and an evaluation apparatus with a test element support for positioning the test element in a measurement position, as well as a measurement and evaluation electronic device. The measurement and evaluation electronic device of the evaluation apparatus comprises a temperature correction device, in order to take into account the temperature prevailing in the measurement zone during the measurement for the determination of the result of the analysis. The temperature correction unit includes a temperature history imaging device for the currentless tracing of the temperature history before the time of measuring, without consuming electric energy before the time of measuring.

11 Claims, 3 Drawing Sheets

TEST ELEMENT ANALYSIS SYSTEM

The invention relates to a test element analysis system for the analytical investigation of a sample, in particular a body fluid, of human beings or of animals. The system comprises two components, namely test elements, which are, in order to perform an analysis, brought in contact to a sample to be investigated, and in which a measurable change which is characteristic of the analysis takes place in a measurement zone, as well as an evaluation apparatus comprising a positioning unit for positioning a test element in a measuring position, a measuring unit for measuring the characteristic change, and an electronic evaluation device for obtaining a result of the analysis, based on the result of the measurement.

Test element analysis systems are common in medical science, in particular for the analysis of blood and urine. In most cases, the test elements have the form of test strips. Other forms of test elements are, however, also common, e.g. flat, essentially square plates.

Generally the test elements contain reagents the reaction of which with the sample leads to a detectable change of the test element; this change is measured with the evaluation apparatus belonging to the system. Very common are photometric analysis systems, in which the reaction causes a color change in a detection layer of the test element. The color change is then measured photometrically. Electrochemical analysis systems are also of important significance. In these, an electrically measurable change of the test element occurs due to the reaction. Apart from these analysis systems working with reagents, reagent-free analysis systems are discussed, too. In these, an analytically characteristic property (e.g. the light absorption spectrum) of the sample itself is measured after contacting the test element with the sample. The invention is generally suitable in combination with all these procedures.

Test element analysis systems are used in medical laboratories. The invention is, however, particularly intended for applications in which the patients themselves perform the analysis in order to monitor their health state (home monitoring). This is of particular medical importance for diabetics, who have to check the glucose concentration in their blood several times a day in order to adjust the insulin injections. For such applications, the evaluation apparatuses must be lightweight, small, battery-operated, inexpensive and robust.

A fundamental problem is due to the fact that the measured quantity which is characteristic for the analysis, is in many cases very temperature-dependent. This temperature dependence is, in many cases, about one or two percent per degree. In home-monitoring, the exposure of the analysis system to high temperature changes is unavoidable. Temperature variations of at least ±5° have to be taken into account. Much higher temperature variations may occur, if measurements are to be performed under unusual conditions (e.g. in a car or outdoors).

In order to avoid the measurement uncertainties resulting from this, it was proposed to control the temperature of the measuring zone of the test element to a constant value by means of a corresponding constant-temperature unit. For example, U.S. Pat. No. 5,035,862 describes temperature control of individual test fields of urine test strips by means of inductive heating. However, such procedures are, due to their high energy consumption, not practicable for small battery-operated apparatuses.

Some analysis systems use a temperature measurement in order to allow a correction of measurement errors caused by temperature variations. This is commonly achieved by an electrical temperature sensor (e.g. a thermocouple or a thermal resistor). Due to design limitations of commonly used analysis systems, the temperature sensor is located at a place remote from the measuring zone of the test element. It is, therefore thermally separated from the measuring zone, i.e. it is not thermally coupled with the measuring zone, in such a manner that the measured momentary temperature coincides at any time with the actual temperature of the measuring zone. Such a temperature sensor is hereafter called Ambient Temperature Sensor (ATS).

The electronic evaluation device of such systems includes a temperature correction unit, which is adapted to take into account the temperature prevailing at the point of time when the measurement for the determination of the result of the analysis is made. Such a correction requires, however, the coinicidence of the actual temperature in the measuring zone of the analysis element with the momentary temperature measured by the ATS at the time of measuring. This condition is not always given, in particular in home-monitoring systems as the live circumstances of the patient require analyses to be performed at different places and with changing temperature conditions. These temperature variations can cause large deviations of the momentary temperature measured by the ATS as compared to the actual temperature in the measuring zone of the test element.

In order to solve this problem, U.S. Pat. No. 5,972,715 proposes to apply a temperature measurement field, coated with a thermochromic liquid crystal (TLC), at the support of the test element in the evaluation apparatus, or at the test element itself. The temperature of the TLC is obtained by a photometric measurement. The difference between the measured temperature and the actual temperature in the measuring zone are said to be minimized by locating the temperature measuring point in close vicinity to the measuring zone of the test element. This can, however, only be achieved with sufficient exactness if the test element itself is coated with the TLC. This leads to considerable additional cost for the production of the test elements. Furthermore, an acceptable exactness of the temperature measurement can only be obtained with expensive measurement equipment.

It is an object of the invention to provide an analysis system which allows an increased measurement accuracy by an improved temperature compensation. This shall be achieved in a way which complies with the requirements of home-monitoring systems. In particular, this improvement shall not lead to a significant increase of the weight, the size or the battery consumption of the evaluation apparatus.

With an analysis system of the previously described type, this problem is solved by the fact that the temperature correction unit includes a temperature history imaging device, which traces the temperature history preceding the time of the measurement in a currentless manner, i.e. without using electric energy up to the time of measurement.

The temperature history imaging device allows to take into account, in the evaluation of the measurement signal and calculation of the result of the analysis, the temperature history in the vicinity of the apparatus before the point of time in which the measurement is made. This provides a substantially improved information about the actual temperature in the area of the measurement zone of the test element. If, for example, the evaluation apparatus was brought from a cold ambient (e.g. a car parked outdoors at a temperature of 10° C.) into a considerably warmer ambient (e.g. a living room with a temperature of 20° C.), this large temperature increase is indicated by the temperature history imaging device. In this case, it must be assumed that the momentary temperature indicated by an ATS does not correspond to the actual ambient temperature (thus, there is no thermal equilibrium to the ambient). The temperature in the measuring zone of the test element follows ambient temperature changes much faster than an ATS fixed in the apparatus housing, because the heat transfer from the ambient to the test zone is relatively good and the heat capacity of the test element is relatively small. The corresponding delay of the momentary temperature measured in the apparatus as compared to the actual temperature of the measurement zone, can be estimated using the output of the temperature history imaging device and corresponding empirical vales, programmed into the electronic evaluation device. On the basis of this information, the result of the analysis can be corrected, or—if a correction is not possible due to excessive temperature changes—the calculation of the result of the analysis can be interrupted, outputting an error signal.

An essential characteristic of the invention is the fact that no electric energy is consumed during the period to which the temperature history refers. A temperature history imaging device which operates in this sense "currentless" can be provided at very low cost. Hereafter it will be called System Temperature History Device(STHD).

The system of the invention is, in particular, better appropriate for the home-monitoring analysis than a system described in U.S. Pat. No. 5,405,511, which measures the temperature electrically by an ATS in regular intervals and determines on the basis of the sequence of measured temperatures a corrected temperature by extrapolation. This requires to make temperature measurements for a sufficiently long period before the analysis, either continuously or in predetermined intervals. In order to avoid a waiting time before the performance of a test, temperature measurements are also performed, in intervals of several minutes, when the apparatus is switched off. This allows to perform the extrapolation to the correction temperature immediately after switching on the apparatus. The drawback, however, is an increased battery consumption, as the electronic system of the apparatus must be repeatedly operated in intervals of only a few minutes in order to determine the temperature.

The STHD can be embodied in different ways. For example, a temperature-sensitive liquid crystal chip, being in thermal contact to a bigger thermal mass (e.g. glued onto a metal body) may be used. In this case the imaging of the temperature history is based on the fact that changes of the ambient temperature lead in different zones of the chip to different rates of the color change of the liquid crystals. These color changes can be photometrically measured.

Another embodiment is, however, simpler and therefore preferable, in which the STHD includes a thermal mass and a plurality of electric temperature sensors which are located in different places. At least one temperature sensor designated as Temperature History Sensor (THS) is located inside the thermal mass. The thermal mass is formed by a solid body with a high and constant heat capacity. It is heat-insulated in the evaluation apparatus, i.e. as completely as possible thermally insulated from all other constructive elements of the device, so that its temperature depends, as far as possible, only on the heat exchange with the ambient air taking place at the surface of the thermal mass.

According to a preferred design, a temperature sensor belonging to the STHD, hereafter designated as Reference Temperature Sensor (RTS), is located near the thermal mass—but without direct contact to it—in a way that it measures the temperature of the ambient air in the vicinity of the thermal mass. This temperature sensor can simultaneously serve as ATS of the temperature correction device. In this embodiment, the function of the STHD is based on the comparison of the temperature measured inside the thermal mass with the temperature of the ambient air in its vicinity. If both temperature values coincide, it can be assumed that the ambient temperature has not changed in the period preceding the measurement. If the temperature of the thermal mass is smaller than the ambient temperature, it can be assumed that the temperature rose before the time of measurement. In the opposite case (thermal mass warmer than ambient temperature) the temperature has fallen.

For this embodiment, the material of the thermal mass is preferably chosen such that the heat transfer inside the thermal mass which is determined by the thermal conductivity of its material, is fast, compared to the heat transfer between the ambient temperature and the thermal mass. For the majority of typical solid materials, in particular for metals, but also for plastics, this condition is complied with, as the thermal conductivity of these materials is high in comparison to the heat exchange with the ambient air taking place at their surface. Therefore, most solids are isothermal heat storage elements. A significant temperature gradient can only be established at the surface of such solid materials, whereas internal temperature gradients in the bulk of such materials are so small that they can only be measured with very sophisticated equipment.

It is, however, also possible to make the thermal mass from a material having a thermal conductivity which is so small that changes of the ambient temperature lead to temperature gradients in the interior of the thermal mass which can be measured with sufficient accuracy at tolerable technological expense. Materials which comply with this condition, and which have, at the same time, a sufficiently high thermal capacity, are e.g. highly porous insulator materials, for example porous glass or ceramic materials. If such a material is used for the thermal mass, preferably at least two temperature sensors of the STHD are in contact with the thermal mass. The difference of the temperature outputs of these temperature sensors is an indication of the change of the ambient temperature before the time of measurement. With other words: For such a STHD, the spatial temperature gradient in the thermal mass, resulting from the change in time of the ambient temperature, provides an information about the temporal temperature history before the point in time at which the measurement is made. To this end it is favorable to locate one of the temperature sensors in the vicinity to the boundary layer of the thermal mass in contact with the ambient air. This sensor is designated as Mass Boundary Layer Sensor (MBLS). The second sensor (THS) should be located as far away as possible from this boundary layer, in the bulk of the thermal mass.

The invention is subsequently described in more detail with reference to embodiments shown in the figures. The described features can be used individually or in combination in order to create preferred embodiments of the invention.

Figure 1:
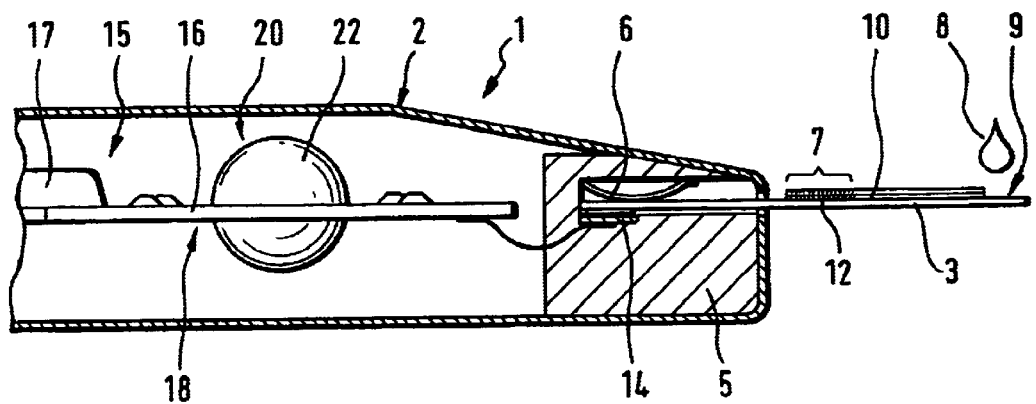
FIG. 1 shows a partial sectional view of an analysis system according to the invention.

The analysis system shown in FIG. 1 consists of an evaluation apparatus 2 and of single use (disposable) test elements 3.

The evaluation apparatus 2 has a test element support 5 for fixing a test element 3 in the measuring position shown in FIG. 1. The test element 3 is fixed in the measuring position by appropriate means, as e.g. a leaf spring 6.

For performing a measurement, sample liquid is transported to a measurement zone 7 of the test element 3. In the embodiment shown, this is accomplished by contacting a blood drop 8 to a sample application zone 9, located at an end of the test element 3, from which it is suctioned to the measurement zone 7 through a capillary gap 10. A reagent layer 12, which is dissolved by the sample liquid and reacts with its components, is located in the measurement zone 7.

The reaction leads to a measurable change in the measurement zone 7. In the represented case of an electrochemical test element, the measurement of an electrical quantity is performed by means of electrodes located in the measurement zone, not shown in the figure. In the measuring position, a contact is made between the electrodes of the test element 3 and terminal contacts 14 of the test element support 5. The terminal contacts 14 are connected to a measuring and evaluation electronic device 15, highly integrated for compact design and high reliability. In the represented case, the electronic device consists mainly of a printed circuit board 16 and a special IC (ASIC) 17. So far, the analysis system shown is conventional and does not require further explanation.

Figure 2:
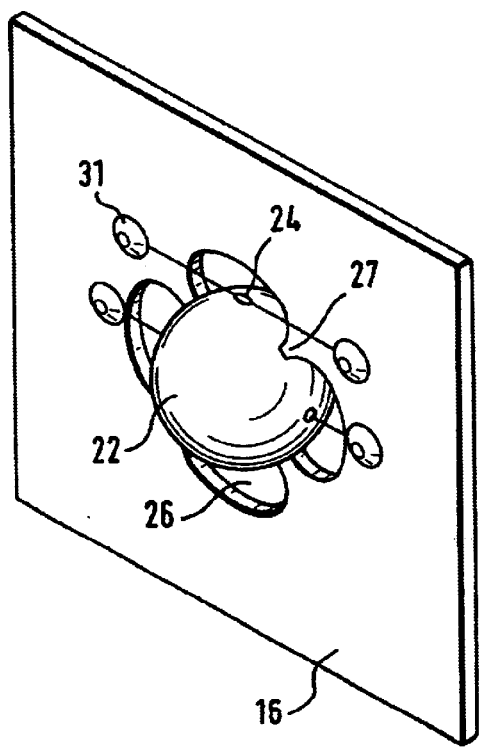
FIG. 2 shows a perspective view of a STHD appropriate for the invention.
Figure 3:
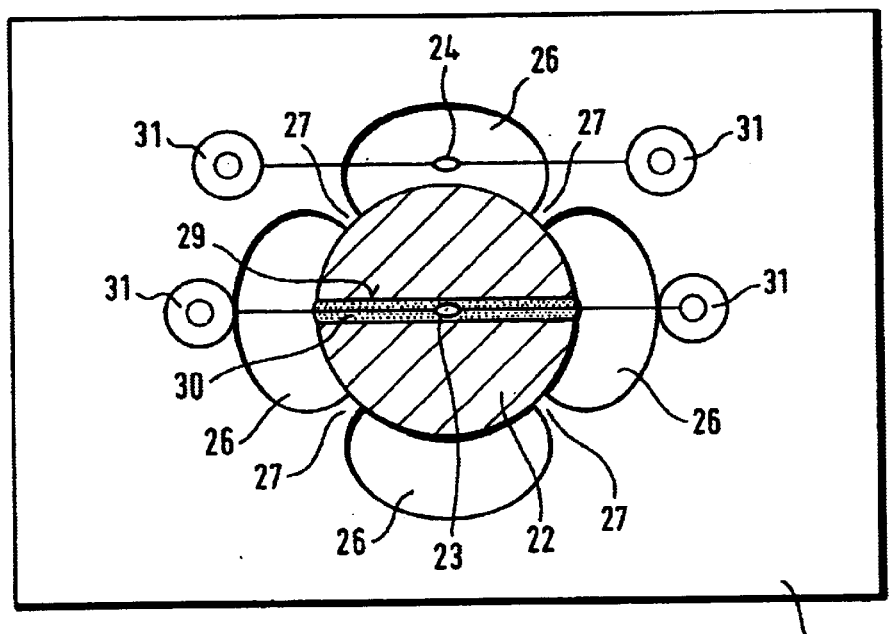
FIG. 3 shows a partial sectional view of the STHD according to FIG. 2.

A component of the electronic measuring and evaluation device 15 is a temperature correction unit 18 comprising a temperature history imaging device STHD 20, shown in more detail in FIGS. 2 and 3. It consists essentially of a spherical thermal mass 22 suspended in a heat insulated manner, a first temperature sensor (THS) 23 located in the center of the thermal mass 22, and a second temperature sensor (RTS) 24, located in the vicinity of the thermal mass 22, but without contact to the thermal mass 22. This RTS is, simultaneously, the ATS of the temperature correction unit. This STHD is an example of the above explained first type, in which the thermal conductivity of the thermal mass 22 is sufficiently high that it forms an isothermal heat storage element. Therefore, the first temperature sensor (THS) can be located at an almost randomly chosen point in the interior of the thermal mass 22. With this design type, the outer shape of the thermal mass 22 is of minor significance for its function.

It is, however, important that the thermal mass 22 is fixed in such a manner that its temperature essentially only depends from the temperature of the ambient air, and that an economic inexpensive production is possible. To this end the thermal mass 22 is in the embodiment shown integrated into a printed circuit board 16; preferably a common printed circuit board 16 is used for the measurement and evaluation electronic device as well as for the STHD. The printed circuit board 16 has recesses 26 located in the vicinity of the thermal mass 26, designed in a way that the thermal mass is touched and supported by only relatively thin fingers 27. Thereby the heat transfer from the printed circuit board 16 to the thermal mass 22 is minimized. The first temperature sensor 23 is located in a bore 29 of the thermal mass 22, which after insertion of the temperature sensor is filled up with cast resin.

The second temperature sensor 24 is freely suspended at its wires in one of the recesses 26. Both sensors 23,24 are connected via contact points 31, to conductor tracks (not shown) of the printed circuit board 16.

In a practical embodiment, the thermal mass 23 was formed by an aluminum ball having a diameter of 6 mm and being fixed in a printed circuit board made of plastic of 0.8 mm thickness, as represented in the figure. Thermistors with a diameter of 0.25 mm and with conductor wires of a thickness of 0.025 mm were used as temperature sensors.

Figure 4:
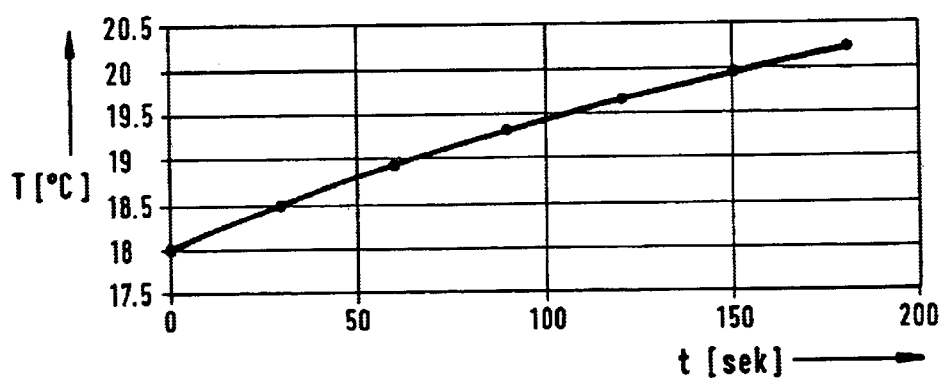
FIG. 4 shows a graphical representation of the temporal change of the measured value of a THS in the interior of a thermal mass for an embodiment according to FIGS. 2 and 3.

The thermal response of such a system, in case of a sudden temperature change from 18° C. to 22° C., is represented in FIG. 4. The abscissa shows the time in seconds and the ordinate shows the temperature in degree C. It becomes apparent that the temperature change occurring within three minutes is easily measurable. Thus, the comparison between the temperatures measured with the THS 23 and the RTS 24 allows valid conclusions with respect to temperature changes in the past. By choosing the size of the thermal mass the rate of temperature change of the STHD can be adjusted in a way that it corresponds to the measuring situation of the analysis apparatus. The time constant of the temperature change of the STHD should approximately correspond to the time constant of the delay of the temperature change of the ATS with respect to the temperature of the measurement zone.

For the embodiment shown, a single temperature sensor 24 forms, on the one hand, the ATS of the temperature correction unit, and, on the other hand, the RTS of the STHD. This is cost-effective and, thus, favorable. In principle, it is, however, possible to supply an ATS in another location of the apparatus, independent from the STHD.

Figure 5:
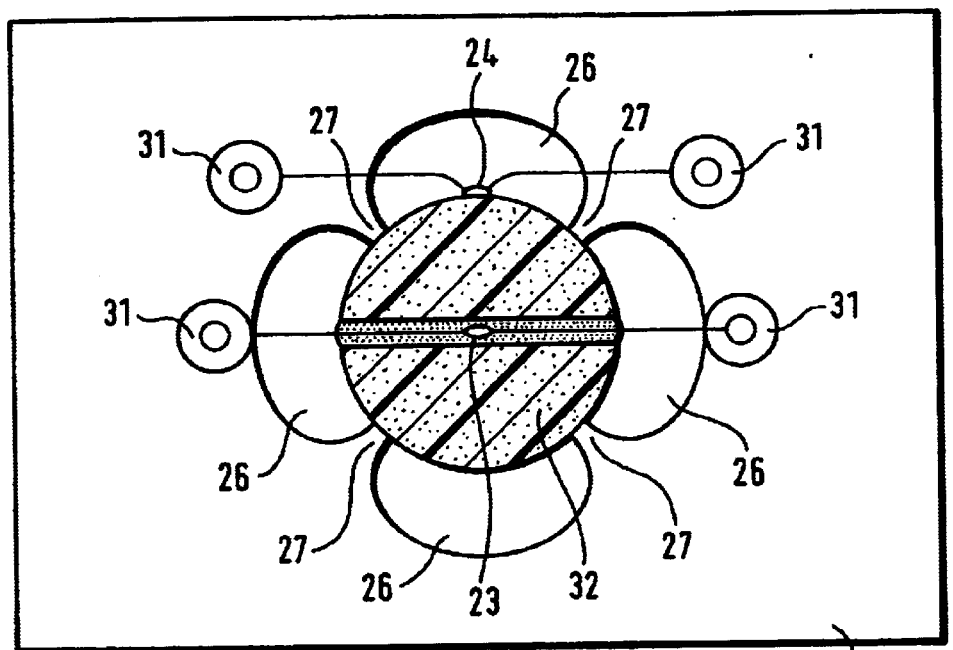
FIG. 5 shows a partial sectional view of an alternative design of a STHD.

FIG. 5 shows an embodiment of the STHD which corresponds to the above mentioned second type, the thermal mass of the STHD of which has a very low thermal conductivity, and, at the same time, a sufficiently high heat capacity.

For this embodiment it is important that the THS 23, fixed in the interior of the thermal mass, is positioned in such a manner that the distance between the sensor and all points of the boundary surface of the thermal mass 32, which are not isolated from the ambient air, is essentially the same. In the represented case, in which the thermal mass is spherical and is in thermal contact with ambient air with almost its entire surface, this means that the THS should be located in the center of the thermal mass.

Here, a MBLS 24 is arranged at the surface of the thermal mass 32. Temperature variations in the ambient of such a STHD lead to the formation of spatial temperature gradients in the interior of the thermal mass 32; these are registered with two or more temperature sensors distributed in or at the thermal mass, enabling a very detailed tracing of the temperature history preceding the point of time at which the measurement is made, without consuming electric energy in the time before the measurement.

Figure 6:
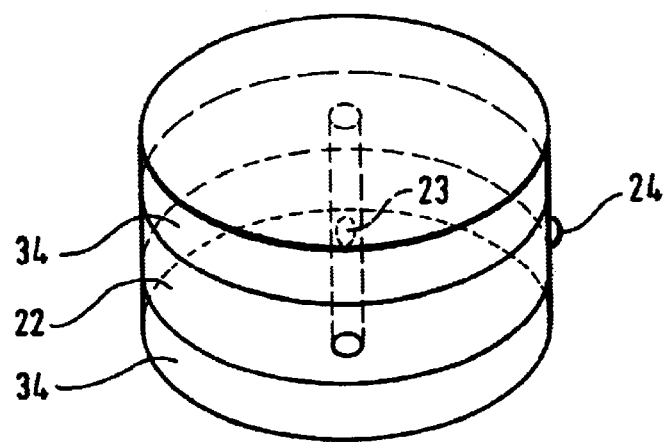
FIG. 6 shows a schematic representation of an alternative shape of a thermal mass.

The mentioned condition to keep a uniform distance between the THS 23 and the points on the surface which are not thermally insulated, can be fulfilled in different ways. For example, FIG. 6 shows a schematic sketch of a design in which the thermal mass is shaped as a disk; the flat sides of the disks are thermally insulated from the ambient air by insulating elements 34, and the THS is located in the center of the disk.

What is claimed is:

1. An analysis system for an analytical investigation of a sample, in particular of a body fluid, the system comprising:

a test element for performing analysis of the sample when brought into contact with the sample, such that after contact with the sample a measurable change occurs in a measuring zone of the test element, wherein the measurable change is characteristic for the analysis;

an evaluation apparatus having a test element support for supporting the test element and an electronic device for measuring the measurable change;

wherein the electronic device comprises a temperature correction unit having an ambient temperature sensor, for determining the ambient temperature prevailing in the measurement zone at the time of measuring the measurable change, wherein the temperature sensor is connected to the electronic device to correct measurement errors caused by temperature variations, wherein the temperature sensor is located remote from the measurement zone;

wherein the temperature correction unit further comprises a temperature history imaging device for curentless tracing a temperature history of the test element before the time of measuring the measurable change in the measuring zone, such that such tracing is conducted without use of electricity; and wherein the temperature history imaging device includes a thermal mass that is suspended in the evaluation apparatus and thermally insulated from the evaluation apparatus, and a plurality of temperature sensors located at different positions relative to the thermal mass.

2. The system of claim 1, wherein one of the temperature sensors of the temperature history imaging device is located in the interior of the thermal mass.

3. The system of claim 2, wherein the temperature sensor located in the interior of the thermal mass is located in the center of the thermal mass.

4. The system of claim 1, wherein output of at least two of the a plurality of temperature sensors of the temperature history imaging device are compared for tracing the temperature history before the time of measurement of the measurable change in the measuring zone.

5. The system of claim 1, wherein a second temperature sensor of the temperature history imaging device is located such that it does not contact the thermal mass.

6. The system of claim 5, wherein the second temperature sensor also operates as the ambient temperature sensor.

7. The system of claim 1, wherein the thermal conductivity of the thermal mass is such that changes in ambient temperature lead to measurable temperature gradient in the thermal mass, wherein the gradient form an image of the ambient temperature history before the time of measurement of the measurable change in the measuring zone.

8. The system of claim 7, wherein at least two temperature sensors from the plurality of temperature sensors of the temperature history imaging device are located in contact with the thermal mass.

9. The system of claim 8, wherein one the at least two temperature sensors is located on a surface of the thermal mass.

10. The system of claim 1, wherein the thermal mass is spherical, such that the surface of the thermal mass is not insulated from ambient air.

11. The system of claim 1, wherein the thermal mass is disk shaped, such that flat sides of the disk are thermally insulated from the ambient air.

* * * * *